United States Patent [19]
Ognier

[11] Patent Number: 5,918,844
[45] Date of Patent: *Jul. 6, 1999

[54] SUPPORT DEVICE FOR MEDICAL OR SURGICAL INSTRUMENT

[76] Inventor: Jean-Francois Ognier, Aulhac, 15240 Saignes, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/632,509

[22] PCT Filed: Oct. 20, 1994

[86] PCT No.: PCT/FR94/01225

§ 371 Date: Jun. 21, 1996

§ 102(e) Date: Jun. 21, 1996

[87] PCT Pub. No.: WO95/10985

PCT Pub. Date: Apr. 27, 1995

[30] Foreign Application Priority Data

Oct. 21, 1993 [FR] France ................................. 93 12779

[51] Int. Cl.[6] ....................................... E04G 3/00
[52] U.S. Cl. ................... 248/276.1; 248/288.51; 269/74
[58] Field of Search ..................... 248/159, 160, 248/158, 274.1, 276.1, 288.51; 269/74

[56] References Cited

U.S. PATENT DOCUMENTS

| | | | |
|---|---|---|---|
| 2,533,494 | 12/1950 | Mitchell, Jr. | 248/160 |
| 3,638,973 | 2/1972 | Poletti | 248/276.1 X |
| 3,986,692 | 10/1976 | Kinoshita . | |
| 4,143,652 | 3/1979 | Meier et al. . | |
| 4,767,231 | 8/1988 | Wallis | 248/276.1 X |
| 4,867,404 | 9/1989 | Harrington et al. . | |
| 5,104,103 | 4/1992 | Auchinleck et al. | 248/276.1 X |
| 5,348,259 | 9/1994 | Blanco et al. | 248/160 X |

FOREIGN PATENT DOCUMENTS

| | | |
|---|---|---|
| 0 167 345 A1 | 1/1986 | European Pat. Off. . |
| 0 415 417 A3 | 3/1991 | European Pat. Off. . |
| 0 486 999 A3 | 5/1992 | European Pat. Off. . |
| 2 339 936 | 8/1977 | France . |
| 25 14 496 A1 | 10/1975 | Germany . |

Primary Examiner—Derek J. Berger
Attorney, Agent, or Firm—Oliff & Berridge, PLC

[57] ABSTRACT

An assembly for attaching a holder to an operating table is connected to a supporting assembly for a medical or surgical instrument via an arm. At least one proximal portion of the arm includes a series of balls and alternately arranged cylindrical members forming ball sockets. A system for axially compressing the arm uses fluid pressure to prevent the balls from rotating in the respective sockets and to lock the medical or surgical instrument in its holder.

10 Claims, 5 Drawing Sheets

SUPPORT DEVICE FOR MEDICAL OR SURGICAL INSTRUMENT

A great many medical or surgical interventions necessitate the use of several instruments which cannot be manipulated by just one individual. Such is especially the case in endoscopy or coelioscopy interventions.

It is therefore necessary to involve several operators, even if the function performed by some of the operators is very minor and consists simply in holding an instrument in a defined position. Apart from the fact that this operation is of little interest for an assistant to carry out, the presence of the assistant causes considerable inconvenience on account of the confined space in the medical operating theatres or units, and it is for this reason that it has been envisaged to use apparatuses which support instruments.

At present there are brackets which are fixed on the operating table and which can be adjusted by means of nut and screw systems. On account of the necessary manipulations of the blocking means, the adjustments are difficult and long, which means that any advantage of this type of apparatus is lost.

It has been envisaged to use devices having a flexible arm, for example having rings lying with friction one upon the other (of the flexible shower type). However, such devices do not permit a precise positioning and they do not remain in the position given to them when a force is exerted.

The documents EP-A-0,167,345 and U.S. Pat. No. 4,930,932 each concern a device including means, for attachment to an operating table or the like, which means are connected to means for supporting a medical or surgical instrument via an arm, in which at least one proximal segment of the arm consists of a succession of balls and cylindrical elements serving as socket seats for the balls and arranged alternatingly, means for axial compression of the arm being provided in order to ensure, by means of pressure, that the balls are blocked in rotation on their socket seats, these tensioning means also ensuring that the medical or surgical instrument is blocked in its support and being controlled from the distal end of a demountable distal segment of the arm.

However, such a device possesses a moderate rigidity in the blocking position and it has the disadvantage of necessitating a large number of balls, since the fact that the blocking cable passes through each of them considerably limits their angular clearance.

The document EP-A-0,415,417 discloses a retractor of the type including means, for attachment to an operating table or the like, which means are connected to means for supporting a medical or surgical instrument via an arm, in which at least one proximal segment of the arm consists of a succession of balls and cylindrical elements serving as socket seats for the balls and arranged alternatingly, means for axial compression of the arm being provided in order to ensure, by means of pressure, that the balls are blocked in rotation on their socket seats, the means for axial compression of the arm comprising means for supplying pressurized fluid to all the cylindrical elements each associated with a ball, and the means for releasing the axial compression of the arm including a manoeuvering member, situated at the distal end of the distal segment of the arm, that is to say in proximity to the support of the instrument holder.

An object of the invention is to make available a support device which ensures perfect immobilization of the instrument after positioning, including when the instrument is subjected to an external force. Another object is to allow the practitioner to adjust and block the device instantly, using only one hand.

Another object is to produce a device possessing all the degrees of freedom within the operating area.

Another object is to permit a dismantling of the support from the instrument in order to carry out sterilization thereof.

These various objects are achieved by means of a support device of the type disclosed by the document EP 0,415,417, and in which the arm includes a proximal rigid segment and a distal rigid segment, the proximal segment including only two balls, one at each of its ends, namely a proximal ball integral with the means for attachment of the arm to the operating table or the like, and an intermediate ball connecting the proximal segment to the distal segment, the distal segment being demountable and bearing, at its distal end, a distal ball serving as a medical or surgical instrument holder, and the means for axial compression of the arm also ensure the blocking of the distal ball.

According to one embodiment of the invention, each ball is associated with a socket seat consisting of a ring forming a piston which is movable in a recess, forming a cylinder, of the associated end of the corresponding cylindrical element.

The means for releasing the axial compression of the arm and of the distal ball advantageously consist of a flap valve for escape of the pressurized fluid, and a member for mechanically manoeuvering this flap valve, situated at the distal end of the distal segment of the arm.

According to one simple embodiment of the invention, the pressurized fluid participating in the axial compression of the arm is compressed air, each operating theatre or treatment room normally being equipped with a source of compressed air. In this case, the socket seat of the proximal ball, nearest the proximal end of the proximal segment of the arm, advantageously consists of a ring forming a piston, the cylinder arranged at the corresponding end of the first cylindrical element being connected permanently to a compressed air source, while the socket seat of the intermediate ball, furthest from the proximal end of the proximal segment of the arm, consists of a ring forming a piston, the cylinder arranged at the corresponding end of the cylindrical element situated at the distal end of the proximal segment of the arm being connected, via a central conduit, to the aforementioned cylinder accommodating the socket seat ring forming the piston of the proximal ball, this same cylinder accommodating a second piston or auxiliary piston mounted in opposition to the first in such a way as to be constantly driven back by the compressed air in the direction of the distal end of the distal segment of the arm, and to transmit to the socket seat ring forming the piston of the distal ball or instrument holder ball, by way of a tubular piece forming a spacer, the axial force necessary for blocking this distal ball.

In order to allow the practitioner to unblock instantly the three balls of this arm without having to interrupt the supply of compressed air to the proximal end of the arm, according to one advantageous embodiment of the invention there is provided, on the one hand, in the auxiliary piston, an axial channel which is equipped with a flap valve normally held in the closure position by the pressure of the compressed air, and, on the other hand, at the distal end of the distal segment of the arm, that is to say in the vicinity of the instrument holder ball, a lever for controlling the release of the compressed air to the environment, this lever being linked to a rod which is axially movable, in the direction of the aforementioned flap valve, so as to control the opening thereof and in so doing to bring the aforementioned cylinder, which accommodates these two pistons, into communication with the inside of a tubular central part of this distal segment of the arm, the said central part communicating with the outside via radial holes and axial slots arranged for this purpose in this distal segment of the arm.

Finally, according to yet another advantageous characteristic of the invention preventing inadvertent unblocking of the medical or surgical instrument in its support ball, on the one hand, the socket seat ring forming the piston, and normally ensuring the blocking of this ball, has associated with it a spring means which acts on this socket seat ring in the same direction as the compressed air, and, on the other hand, the socket seat of this distal ball opposite the socket seat on which the auxiliary piston acts, that is to say the socket seat situated at the distal end of the distal segment of the arm, consists of the inner end of a tubular screw which is screwed into the distal end of the distal segment of the arm which, for this purpose, is tubular and has an internal screw thread.

Thus, the operation of releasing to the environment the compressed air ensuring the blocking of the two segments of the arm does not completely free the medical or surgical instrument from its instrument holder ball. Thus, the practitioner can displace the instrument by deformation of the arm, without necessarily risking inadvertently displacing the instrument in its instrument holder ball. If he wishes to proceed with a displacement of the instrument in its ball, he can do this after he has activated the release of the compressed air to the environment. To do this, it suffices for him to unscrew the tubular screw which constitutes that socket seat of the instrument holder ball situated at the distal end of the distal segment of the arm.

Trials have demonstrated that this support device should be able to withstand a force, at the distal end of the arm, of the order of 50 N, a force which adds to the weight of the arm and of the instrument. The proximal ball should be able to resist a torque of 50 N.m. Since this resistance is based on the friction between the balls and their socket seats, a friction whose yield, taking into consideration the coefficient of metal/metal friction, is of the order of 10%, it is necessary to develop a bearing force of the movable socket seat on the proximal ball equal to 10,000 N for a ball of 50 mm diameter, and consequently a pressure of 51 $10^5$ Pa.

Now, the usual pressures in compressed air distribution systems, generally less than 8 $10^5$ Pa, do not permit the requisite forces to be developed without considerably increasing the dimensions of the devices.

In order to permit these dimensions to be limited to reasonable values, according to one improved embodiment of the invention, each socket seat ring forming the piston of the proximal and intermediate balls of the arm has associated with it at least one secondary piston, having the role of force multiplier and acting on the movable socket seat ring in question by way of a second fluid, preferably incompressible, such as hydraulic oil.

It is for this reason that in that end, furthest from the proximal ball, of the movable socket seat ring of the proximal ball there is formed a secondary cylinder which is blind and which is intended to accommodate the head and a part of the rod of the secondary piston associated with this ring, and of which the distal end forms the proximal wall of the working chamber, supplied with compressed air, of this ring, and the space situated between this ring and the base of the cylinder which accommodates it and which surrounds the rod of this secondary piston being filled with secondary fluid.

Thus, as soon as the working chamber, associated with the movable socket seat forming the piston of the proximal ball, is supplied with compressed air, the associated secondary piston moves back, pressurizing the secondary fluid whose action on the movable socket seat ring of the proximal ball adds to that of the compressed air on this ring.

The auxiliary piston possesses a rod which is guided in an axial bore of a first secondary piston, the front face of which constitutes an annular part of that base of the working chamber associated with the movable socket seat ring of this intermediate ball, and of which the rod is guided in an axial bore of a front wall of a second secondary piston provided with a cylindrical skirt, the free edge of which bears against an annular face of the movable socket seat ring of this intermediate ball, oriented in the opposite direction to this ball, the chamber situated between the head of the auxiliary piston and the front face of the second secondary piston and surrounding the rod of the auxiliary piston being filled with the secondary fluid.

Thus, as soon as the working chamber associated with the movable socket seat ring of the intermediate ball is supplied with compressed air, the rod of the associated first secondary piston is driven back in the chamber filled with secondary fluid, situated between the auxiliary piston and the second secondary piston, pressurizing the secondary fluid contained in this chamber.

This results in two effects:

an action of this secondary fluid against the auxiliary piston which acts on the movable socket seat of the distal ball, which action adds to that of the compressed air, multiplying it, an action of this secondary fluid against the second secondary piston which acts on the movable socket seat ring of the intermediate ball in the same direction as the compressed air and which adds to the action of the compressed air, multiplying it.

The invention will at any rate be clearly understood from the following description in which reference is made to the attached diagrammatic drawing which represents, by way of a nonlimiting example, an embodiment of this device.

This device includes means 1 for attachment to an operating table 2, support means 3 for a medical or surgical instrument 4 of the ball type, the connection between the means for attachment to the operating table 2 and the support means 3 for the instrument 4 consisting of a flexible arm 105. The means 1 for attaching the device to the operating table 2 consist of a stirrup 6 provided with a clamping screw 7.

Figure 1:
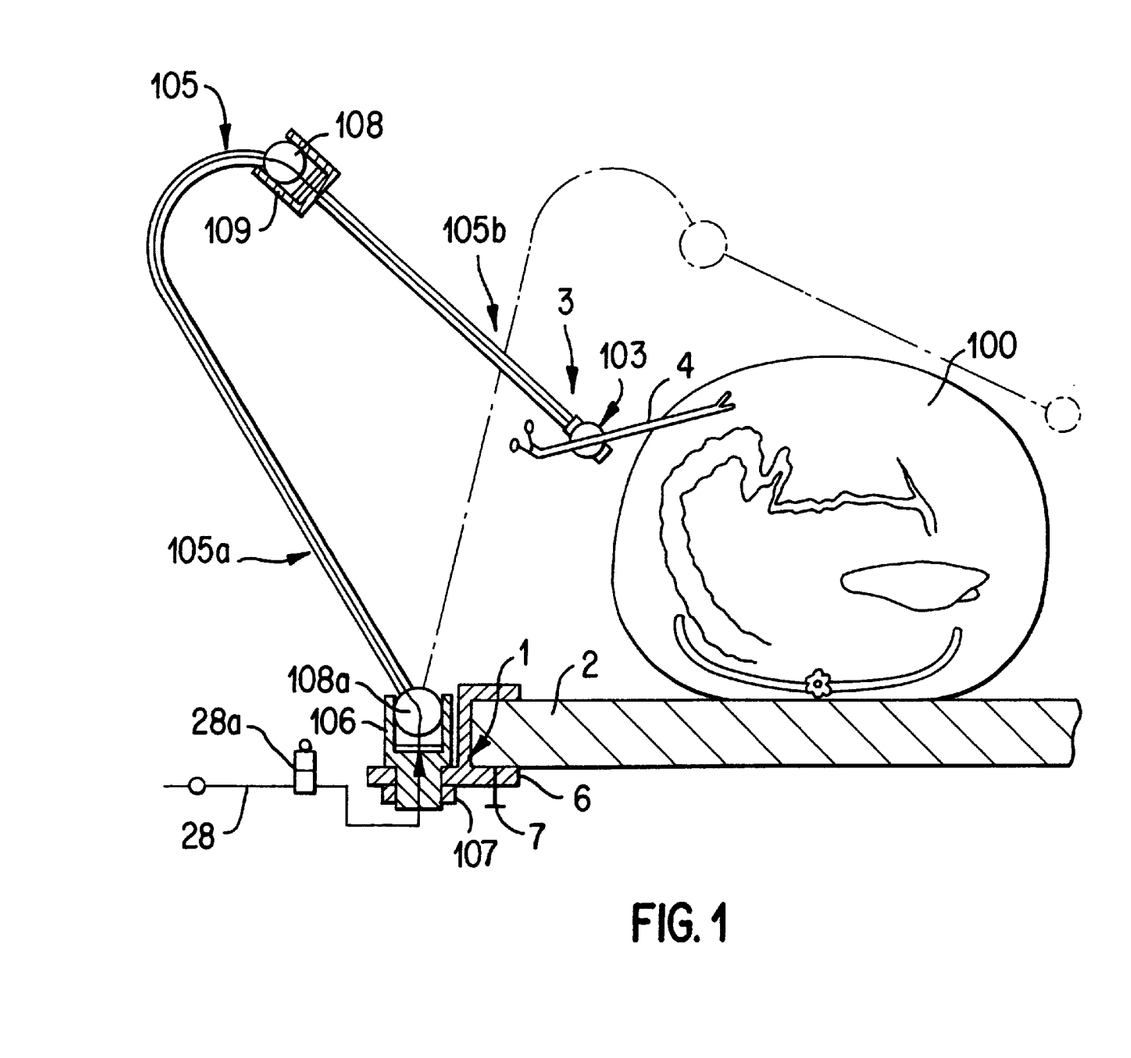
FIG. 1 is an overall view of this device, in the case where the means for axial compression of the cable consist of a tensioning cable.

The means 1 for attaching the arm 105 to the operating table 2 consist of a block 106 provided with a flange 107 integral with the stirrup 6, while the support for the instrument 4 consists of a ball 103 provided at the distal end of the distal segment 105$b$ of the arm 105. As is shown in FIG. 1, the proximal segment 105$a$ of the arm 105 has a first, rigid rectilinear part, integral with a first ball or proximal ball 108$a$, followed by a second, curved part whose free end is connected to the distal segment 105$b$ of this arm 105 via a single intermediate ball 108. The proximal end of the proximal segment 105$a$ of the arm 105 is connected to the support block 106 via the proximal ball 108a. As is shown in FIG. 1, the unblocking of the balls 108a, 108 and 103 allows the practitioner to displace the instrument 4 between the two extreme positions shown in FIG. 1, one on the left of this Figure in solid lines, and the other on the right of this Figure in dot-and-dash lines.

This possibility of manoeuvring the arm 105 from one extreme position to the other, as well as the instrument 4 in its support ball 103, allows the practitioner to approach the organs on which he is to operate, and which are represented schematically by 100 in this figure, in the position which he judges to be the most convenient.

Figure 2:
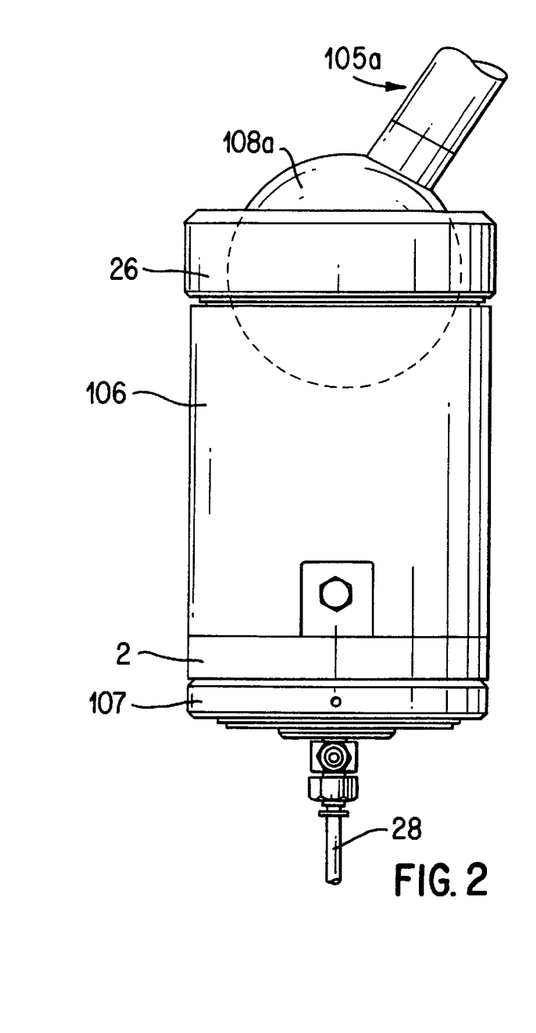
FIG. 2 is a side elevation and FIG. 3 is an axial cross-section, in the plane of FIG. 2, of the proximal end of the arm of this device.
Figure 3:
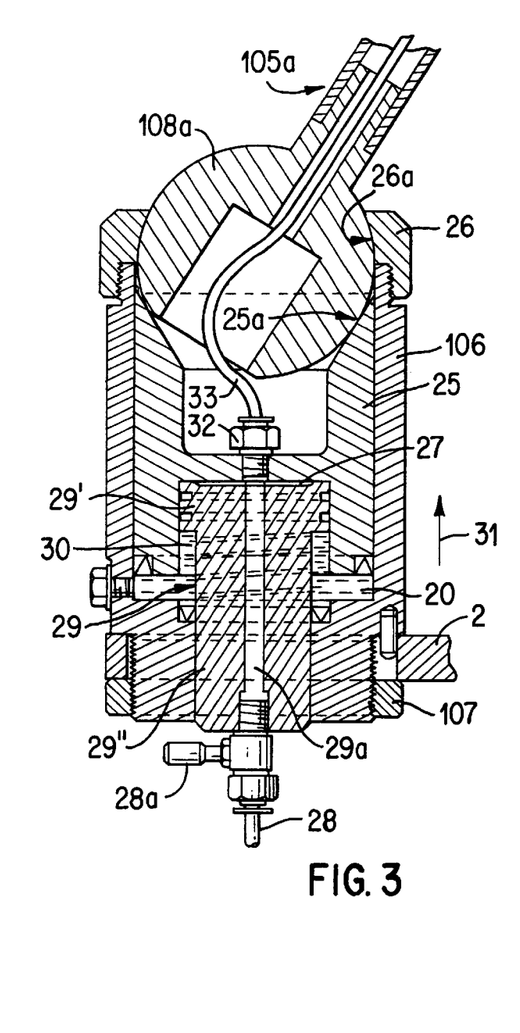
Figure 4:
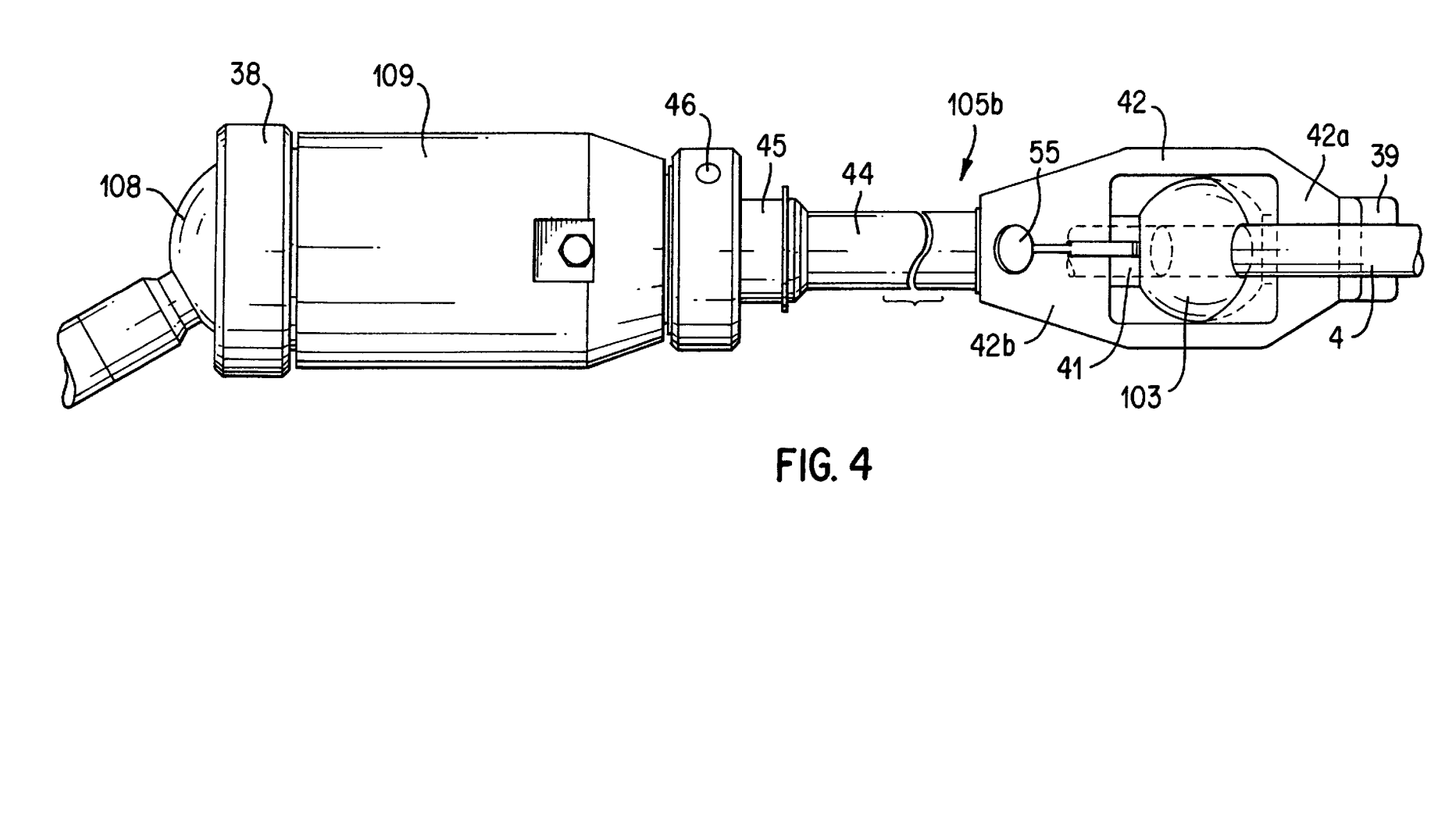
FIG. 4 is a side elevation and FIG. 5 is an axial cross-section, in the plane of FIG. 4, of the distal end of the arm of this device.

FIGS. 2 and 3 show, on an enlarged scale, the proximal end of the arm 105. As can be seen in these figures, the support block 106 of this arm 105 constitutes a cylinder in which there is mounted, so as to be axially movable, a ring 25 whose distal end is configured as a socket seat 25a for the proximal ball 108a. A ring 26 screwed onto the distal end of the support block 106 constitutes the second socket seat 26a of the ball 108a. After mounting, the socket seat 26a of the ball 108a is thus considered as being fixed, whereas its socket seat 25a formed in the ring 25 constitutes its movable socket seat. The working chamber 27 of the jack consisting of the support block 106 and the ring 25 is situated on the proximal side of the latter and is supplied axially via a compressed air inlet conduit 28 connected to an axial channel 29a passing through the proximal end of the support block 106. Mounted between the conduit 28 and the channel 29a there is a nozzle 28a whose function is to limit the flow rate of compressed air upon unblocking of the balls, as is described hereinafter, with a view to limiting the compressed air consumption during this unblocking.

It will be readily appreciated that the supply of compressed air to the chamber 27 provokes the displacement of the ring 25 in the direction of the arrow 31 and, consequently, the blocking of the ball 108 between its two socket seats 25a and 26a.

Figure 5:
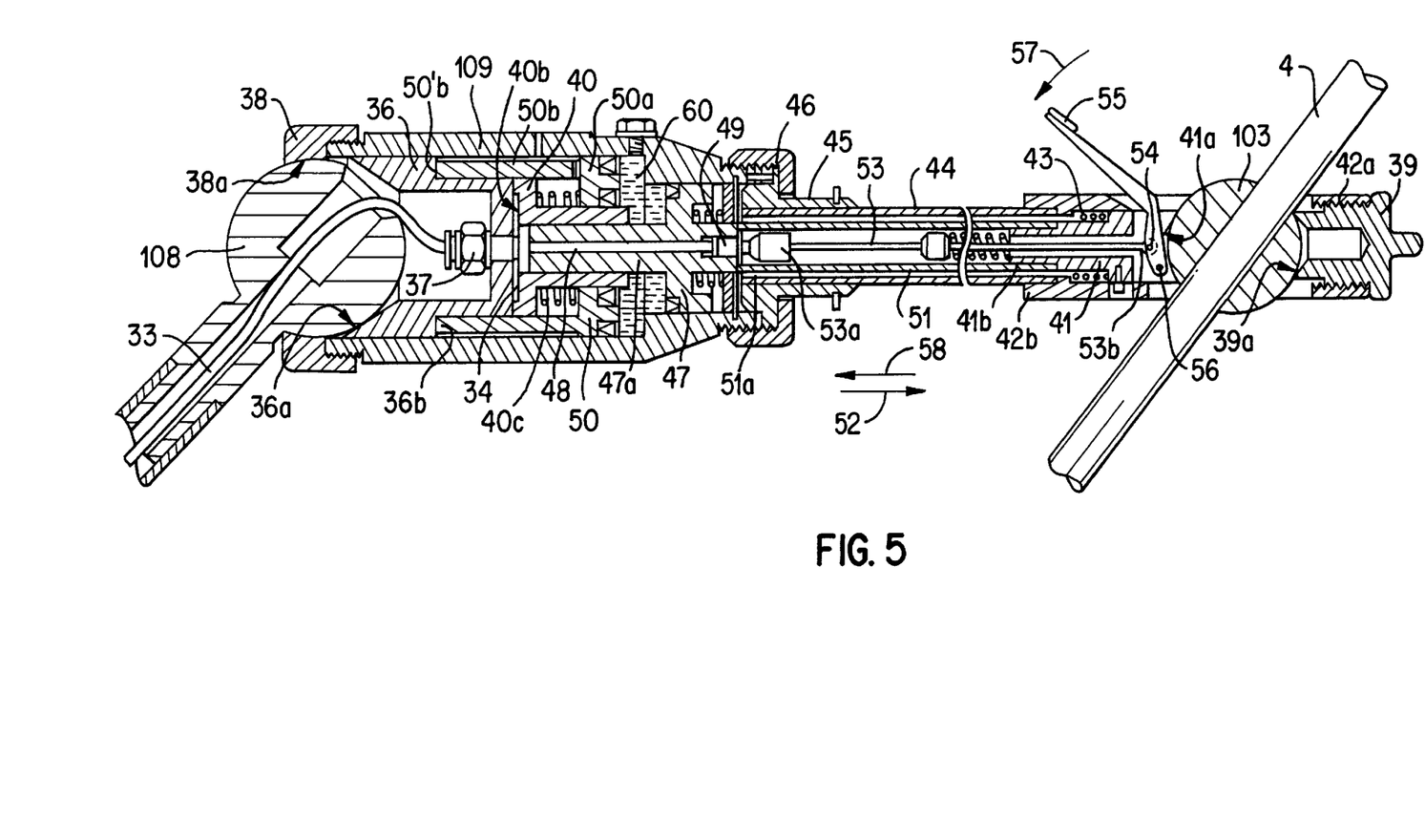

As is shown in FIGS. 3 and 5, the channel 29a for supplying the chamber 27 continues, beyond this chamber, in the form of a connection piece 32 and a flexible conduit 33 passing through the proximal ball 108a and the whole proximal segment 105a of the arm 105, as well as the intermediate ball 108, as far as the working chamber 34 of a jack consisting of a cylindrical element 109 and a ring 36 whose proximal end is configured as a socket seat 36a for the ball 108. In order to penetrate into the working chamber 34, the flexible conduit 33 passes axially through the ring 36 via a connection piece 37. As is shown in FIG. 5, indicating more particularly the intermediate ball 108 and the distal segment 105b of the arm 105, the second socket seat or proximal socket seat 38a of the ball 108 consists of a threaded ring 38 screwed onto the proximal end, threaded for this purpose, of the cylindrical element 109. This socket seat 38a thus constitutes the fixed socket seat of the ball 108, whereas its socket seat 36a constitutes the movable socket seat thereof, permitting the blocking and unblocking of this ball 108.

It will thus be appreciated that when compressed air is introduced into the working chamber 27 associated with the ring 25 in which the socket seat 25a of the first ball 108a is formed, this same compressed air reaches the working chamber 34 of the jack associated with the ring 36 in which the movable socket seat 36a of the intermediate ball 108 is formed. Consequently, the two balls 108a and 108 can therefore be blocked instantly and simultaneously.

As is shown more particularly in FIG. 5, the ball 103 or distal ball serving as a support for the instrument 4 is clamped between a terminal screw 39, at the proximal end of which there is fitted one of the socket seats, or fixed socket seat 39a, of the ball 103, and a socket seat 41a or proximal socket seat is fitted at the distal end of a ring forming a piston 41, the mounting of which, and the function of which, will be described later.

The screw 39 is screwed into a threaded hole arranged at the centre of the distal crosspiece 42a of the distal end 42 of the distal segment 105b of the arm 105 configured as a frame, inside which the ball 103 is accommodated. The piston 41, in which the other socket seat 41a of the ball 103 is fitted, is mounted so as to slide axially through the second crosspiece or proximal crosspiece 42b of this frame-shaped end 42 of the distal segment 105b of the arm 105. A spring 43 ensures constant application of the socket seat 41a against the ball 103, after screwing the screw 39 into the distal crosspiece 42a of the frame 42.

After fitting the screw 39, the proximal socket seat 41a constitutes the movable socket seat of the ball 103, while the socket seat 39a constitutes the fixed socket seat thereof.

The proximal crosspiece 42b of the frame 42 is integral with the distal end of a tube 44 whose proximal end is integral with a shouldered sleeve 45 itself flanged at the distal end, threaded for this purpose, of the cylindrical element 109 by means of a nut ring 46. This tube 44 thus constitutes, with the frame 42, the distal segment 105b of the arm 105.

Figure 6:
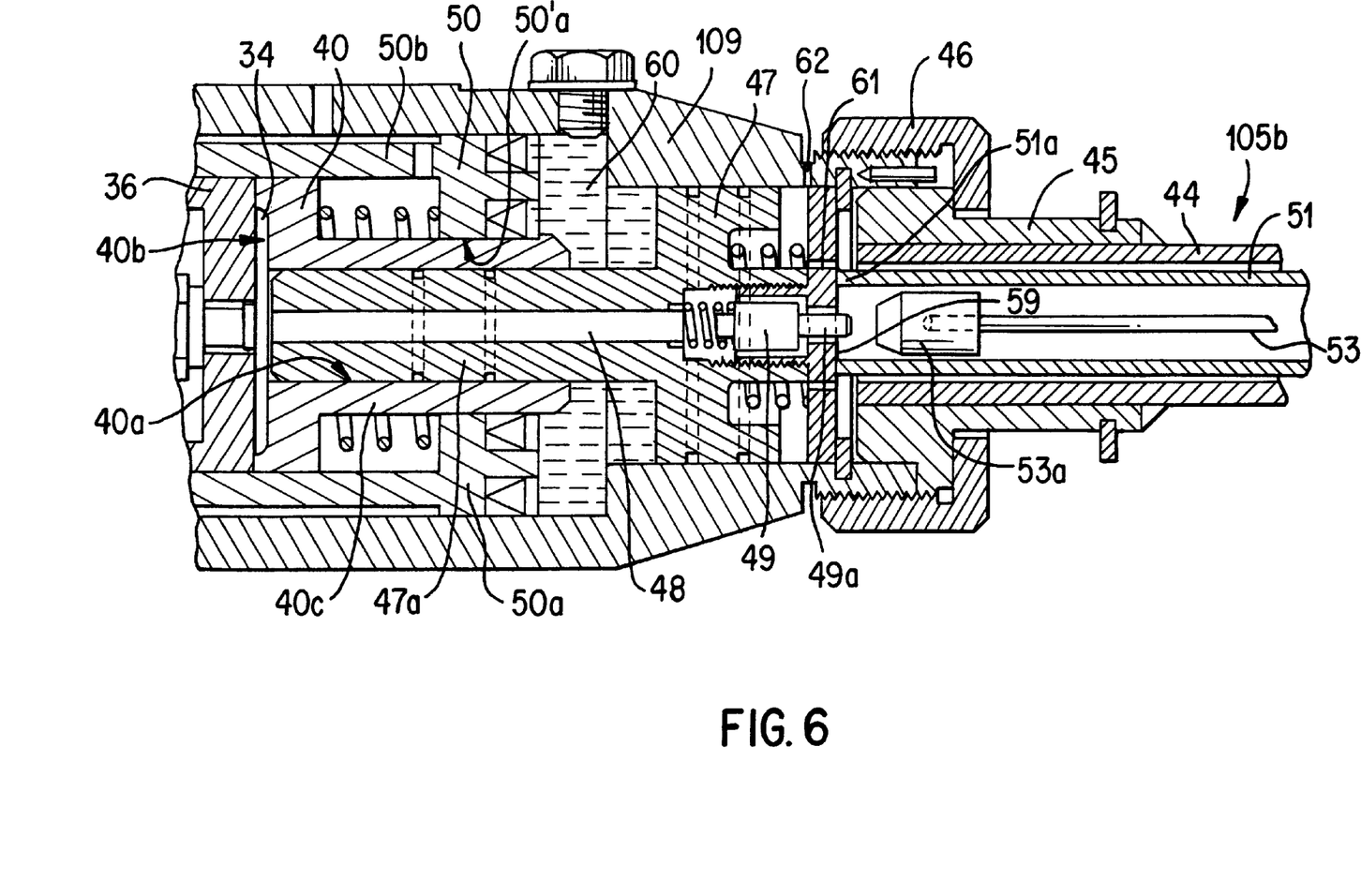
FIG. 6 is, on an enlarged scale, a partial view of FIG. 5, showing the exhaust flap valve which cannot be seen clearly in FIG. 5.

As is evident from an examination of FIGS. 5 and 6, the distal segment 105b of the arm 105 can thus be easily demounted from its proximal segment 105a by simply unscrewing the ring 46.

The base of the chamber 34, associated with the ring 36 in which the socket seat 36a of the intermediate ball 108 is formed, partially consists of the rod 47a of an auxiliary piston 47 mounted with axial sliding in the distal end of the cylindrical element 109. In addition, this auxiliary piston 47 and its rod 47a are axially traversed by a channel 48 which opens out, at its proximal end, into the chamber 34, and of which the distal end is closed by a flap valve 49 normally held in the closure position when the chamber 34, and consequently the channel 48, are supplied with compressed air, which corresponds to the position of blocking of the balls 108a, 108 and 103.

Furthermore, as is shown in FIG. 5, the proximal end of the piston 41, in which the socket seat 41a of the ball 103 is formed, is configured as a rod 41b engaged in the distal end of a tubular piece 51 whose proximal end 51a normally bears against the distal end of the auxiliary piston 47. Consequently, when the chamber 34 is supplied with compressed air, the auxiliary piston 47, which constitutes a part of its base, is displaced axially in the direction of the arrow 52, carrying with it the tubular piece 51 and, consequently, the piston 41 in which the socket seat 41a of the ball 103 is formed. The supply of compressed air to the chamber 34 thus also provokes the blocking of the ball 103.

In order to permit the simultaneous and instantaneous unblocking of all the balls 108a, 108 and 103, a rod 53 is provided which is mounted axially movably inside the tubular piece 51, the proximal end 53a of which is situated very near the manoeuvring rod 49a of the flap valve 49, whereas its distal end 53b is linked, by means of a pin 54, to a control lever 55 which is itself articulated on a pin 56 carried by the piston 43. Consequently, a manoeuvre of the lever 55 in the direction of the arrow 57 has the effect of displacing the control rod 53 in the direction of the arrow 58, counter to the direction of the arrow 52, and, consequently, of manoeuvring the flap valve 49 in the opening direction, the effect of which is to bring the channel 48 into communication with the outside atmosphere. The air can in fact escape beyond the flap valve 49, as far as the bore of the tubular piece 51, and, from there, successively through radial slots 59, axial slots 61 and, once again, radial slots 62, and reach the outside of the cylindrical element 109. As has been indicated previously, when the channel 48 is connected to the outside air by means of manoeuvring the flap valve 49 in the opening direction, the flow rate of air is limited by the nozzle 28a.

Consequently, a simple manoeuvre of the lever 55 by the practitioner can allow the latter to unblock the balls of the arm 105 and to modify the position of the latter until the ideal position is obtained.

However, to ensure that the unblocking of the three balls does not risk causing a loss of adjustment of the position of the instrument 4 in the ball 103 which serves as its support, there is provided in the recess of the proximal crosspiece 42b, which serves to accommodate the piston 41, a return spring 43 which tends constantly to push the piston 41 and, consequently, the socket seat 41a of the ball 103, in the direction of the latter. The complete unblocking of the ball 103, in order to permit a modification of the position of the instrument 4 in this ball 103, can therefore only be obtained by unscrewing the screw 39, at the proximal end of which the socket seat 39a of the ball 103 is formed.

As has been indicated previously, the pressure in the compressed air distribution systems is generally of the order of $8 \cdot 10^5$ Pa. Now, it has been demonstrated that the forces to which the distal ends of the devices for supporting medical or surgical instruments are subjected are of the order of 50 N, which subjects the proximal ball to a torque of the order of 50 N.m. Now, the resistance or moment of the proximal ball, like that of the other balls, is based on the friction between the balls and their socket seats, the yield of which friction, taking into account the coefficient of metal/metal friction, is of the order of 10%. It is therefore necessary to develop a bearing force of the movable socket seat on the proximal ball of the order of 10,000 N for a ball of 50 mm diameter, which is considered a reasonable dimension. Now, this force can result only from a pressure of the order of $51 \cdot 10^5$ Pa. Consequently, in order to make it possible to limit to reasonable dimensions the constituent elements of this support device, there has been provided, in association with each socket seat ring forming a piston of the proximal 108a and intermediate 108 balls, at least one secondary piston acting by way of a secondary fluid on the socket seat ring in question and making it possible to multiply the force generated by the compressed air on this socket seat ring. The secondary fluid is preferably an incompressible fluid such as hydraulic oil.

This is why, as is shown more particularly in FIG. 3 in the case of the proximal ball 108a, the base of the working chamber 27 of the jack consisting of the piston ring 25 and the cylindrical body 106 consists of the head 29' of a secondary piston 29 traversed axially by the compressed air supply channel 29a. This auxiliary piston 29 is movable in a blind cylindrical bore 30 formed coaxially to the ring 25, in its proximal face, that is to say the face furthest from the proximal ball 108a. The space 20 situated between the ring 25 and the base of the cylindrical body 106, and which surrounds the rod 29" of this secondary piston 29, constitutes the working chamber associated with this secondary piston 29 and filled with the secondary fluid, which preferably consists of hydraulic oil.

It will be readily appreciated that as soon as the working chamber 27, associated with the socket seat ring 25 forming the piston of the proximal ball 108a, is supplied with compressed air, the secondary piston 29 which is associated with it tends to retreat, that is to say to be displaced in the direction counter to that of the arrow 31, the effect of which is to pressurize the secondary fluid, whose action on the movable socket seat ring 25 of the proximal ball 108a adds to that of the compressed air on this ring. Taking into consideration the size of the cross-section of the chamber 20 in relation to that of the chamber 27, the force generated by the secondary fluid on the movable socket seat ring 25 is much greater than that generated by the compressed air. In the example illustrated in the drawing, the force developed by the hydraulic pressure is of the order of 5 times greater than that developed by the pneumatic pressure on the ring 25.

Examination of FIGS. 5 and 6 shows that two coaxial secondary pistons 40 and 50 are associated with the movable socket seat ring 36 of the intermediate ball 108. As is shown in the aforementioned figures, the rod 47a of the auxiliary piston 47 is guided in an axial bore 40a of the first secondary piston 40, the annular front face 40b of which constitutes a part of the base of the working chamber 34 associated with the movable socket seat ring 36 of the intermediate ball 108. The rod 40c of this first secondary piston 40 is guided in an axial bore 50'a of a front wall 50a of the second secondary piston 50. This front wall 50a is provided with a cylindrical skirt 50b whose free edge 50'b bears against an annular face 36b of the movable socket seat ring 36 of this intermediate ball 108, which annular face 36b is oriented in the opposite direction to this ball 108. The chamber 60 situated between the head of the auxiliary piston 47 and the front wall 50a of the second auxiliary piston 50 and which surrounds the rod 47a of the auxiliary piston 47 is filled with a secondary fluid which is preferably incompressible, such as hydraulic oil.

Thus, as soon as the working chamber 34 associated with the movable socket seat ring 36 of the intermediate ball 108 is supplied with compressed air, the rod 40c of the first secondary piston 40 is driven back into the chamber 60, pressurizing the secondary fluid which it contains. This results in two effects:

the secondary fluid, under pressure, in this chamber 60 acts against the auxiliary piston 47 which itself acts on the movable socket seat 41a of the distal ball 103, this action adding to that of the compressed air which fills the working chamber 34; in the embodiment represented in the drawing, taking into account the relative dimensions of the elements, the force developed by the hydraulic pressure is of the order of 9 times greater than that generated by the pneumatic pressure;

the hydraulic pressure prevailing in the chamber 60 also acts against the second secondary piston 50 by pressing it against the movable socket seat ring 36 of the intermediate ball 108, in the same direction as the compressed air in the chamber 34, these two actions adding to each other; in the example illustrated in the drawing, the force generated by the hydraulic pressure in the chamber 60 is of the order of 9 times greater than that generated by the compressed air in the chamber 34.

Consequently, the addition of the secondary pistons 29, 40 and 50 thus has the effect of permitting a considerable increase in the forces generated by the compressed air, without having to provide a distribution system for compressed air at a higher pressure than that which is normally available.

The device has been described for the case where the arm comprises two sections only. However, the number of sections could be greater, without departing from the scope of the invention.

I claim:

1. A support device for a medical or surgical instrument, comprising:

means for attachment to an operating table;

means for supporting the medical or surgical instrument;

an arm connecting the means for attachment and the means for supporting, the arm including a distal segment, a proximal segment, a succession of balls and mated cylindrical segments interposed between the attachment means, proximal segment and distal segment, each cylindrical segment seating a corresponding mated ball of the succession of balls;

a socket seat associated with each ball, each socket seat including a ring forming a piston which is movable in the corresponding mated cylindrical segment;

at least one secondary piston; and means for axial compression of the arm, the means for axial compression utilizing pressure to prevent each of the balls from rotating relative to the corresponding mated cylindrical segment, the means for axial compression of the arm including means for supplying pressurized fluid to all of the cylindrical segments, and means for releasing the axial compression of the arm, the means for releasing including a maneuvering member, disposed at a distal end of the distal segment of the arm and adjacent to the means for supporting;

wherein the proximal segment includes only two balls, the two balls including a proximal ball disposed at one end of the proximal segment and an intermediate ball at the other end of the proximal segment, the proximal ball being mounted with the means for attachment and the intermediate ball connecting the proximal segment to the distal segment, the distal segment being detachable, the means for supporting the medical or surgical instrument including a distal ball disposed at the distal end of the distal segment, the means for axial compression of the arm also locks the distal ball, the at least one secondary piston associated with each of the socket seat of the proximal ball and the socket seat of the intermediate ball, and the at least one secondary piston operating as a force multiplier and acting on the associated socket seat by a secondary fluid which is incompressible.

2. The device according to claim 1, wherein the means for releasing the axial compression of the arm and of the distal ball includes a flap valve for releasing the pressurized fluid, wherein the maneuvering member mechanically maneuvers the flap valve.

3. The device according to claim 2, wherein the socket seat associated with the proximal ball includes a proximal one of said pistons, the corresponding cylindrical segment mated with the proximal ball being connected permanently to a compressed air source, while the socket seat associated with the intermediate ball includes an intermediate one of said pistons, the corresponding cylindrical segment mated with the intermediate ball housing an auxiliary piston and being connected, via a central conduit, to the cylindrical segment mated with the proximal ball, the auxiliary piston opposing the intermediate piston so as to be constantly driven by compressed air of the compressed air source in a direction toward the distal end of the distal segment of the arm, the compressed air also being transmitted to the distal ball via a tubular piece forming a spacer so as to lock the distal ball so as to prevent the distal ball from rotating.

4. The device according to claim 3, wherein the auxiliary piston defines an axial channel, the flap valve being disposed at the axial channel, the flap valve being normally held in a closure position by pressure of the compressed air, and the maneuvering member includes a lever controlling the release of the compressed air from the cylindrical segments, the lever being linked to a rod which is axially moveable toward the flap valve so as to actuate the flap valve to an open position, such that when the flap valve is in the open position, the cylindrical segment mated with the intermediate ball communicates with radial holes and axial slots defined in the distal segment of the arm.

5. The device according to claim 1, wherein the pressurized fluid participating in the axial compression of the arm is compressed air.

6. The device according to claim 1, wherein a spring means acts on the ring of the socket seat associated with the distal ball in the same direction as the pressurized fluid, and further including a distal socket seat opposing the socket seat associated with the distal ball, the distal socket seat disposed at the distal end of the distal segment of the arm, the distal socket seat formed by an inner end of a screw which is screwed into the distal end of the distal segment of the arm, the screw being tubular and having an internal screw thread.

7. The device according to claim 1, further including a nozzle for limiting a flow rate of the pressurized fluid mounted on the means for supplying the pressurized fluid.

8. The device according to claim 1, further including a cylinder formed at an end of the piston of the socket seat associated with the proximal ball which is spaced from the proximal ball, the secondary cylinder being blind and accommodating a head and a part of a rod of the at least one secondary piston associated with the ring of the socket seat of the proximal ball, the distal end of the at least one secondary piston forming a proximal wall of a working chamber, supplied with said pressurized fluid, of the ring of the socket seat of the proximal ball, and a space disposed between the ring of the socket seat of the proximal ball and a base of the cylinder and which surrounds the rod of the secondary piston is filled with the secondary fluid.

9. The device according to claim 1, further including an auxiliary piston associated with the intermediate ball, the auxiliary piston including a rod which is guided in an axial bore defined by the at least one secondary piston associated with the socket seat of the intermediate ball, the at least one secondary piston having a front face which forms an annular part of a base of a working chamber associated with the socket seat of the intermediate ball, the at least one secondary piston also having a rod which is guided in an axial bore of a front wall of a second secondary piston provided with a cylindrical skirt, the free edge of the cylindrical skirt of the second secondary piston bears against and opposes an annular face of the ring of the socket seat of the intermediate ball, wherein a chamber disposed between a head of the auxiliary piston and the front wall of the second secondary piston and surrounding the rod of the auxiliary piston is filled with the secondary fluid.

10. The device according to claim 1, wherein the secondary fluid is hydraulic oil.

* * * * *